(12) United States Patent
Soerensen et al.

(10) Patent No.: US 9,428,741 B2
(45) Date of Patent: Aug. 30, 2016

(54) NUCLEIC ACID CONSTRUCT WITH GENE ENCODING AN ARABINOFURANOSIDASE POLYPEPTIDE AND METHODS OF USING SAME

(71) Applicant: Novozymes A/S, Bagsvaerd (DK)

(72) Inventors: Hanne Risbjerg Soerensen, Bagsvaerd (DK); Christel Thea Joergensen, Bagsvaerd (DK); Lars Hylling Christensen, Bagsvaerd (DK); Christian Isak Joergensen, Bagsvaerd (DK); Carsten Hoerslev Hansen, Bagsvaerd (DK); Lene Venke Kofod, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/680,942

(22) Filed: Apr. 7, 2015

(65) Prior Publication Data

US 2015/0210990 A1     Jul. 30, 2015

Related U.S. Application Data

(62) Division of application No. 11/911,683, filed as application No. PCT/DK2006/000213 on Apr. 25, 2006, now abandoned.

(60) Provisional application No. 60/676,115, filed on Apr. 29, 2005, provisional application No. 60/735,661, filed on Nov. 10, 2005.

(30) Foreign Application Priority Data

Apr. 26, 2005  (DK) ................................ 2005 00609
Nov. 10, 2005  (DK) ................................ 2005 01562

(51) Int. Cl.
| | |
|---|---|
| *C07H 15/26* | (2006.01) |
| *C12N 9/24* | (2006.01) |
| *A21D 8/04* | (2006.01) |
| *A23K 1/165* | (2006.01) |
| *A23L 1/03* | (2006.01) |

(52) U.S. Cl.
CPC ............. *C12N 9/2402* (2013.01); *A21D 8/042* (2013.01); *A23K 1/165* (2013.01); *A23L 1/034* (2013.01); *C12Y 302/01055* (2013.01); *Y02E 50/16* (2013.01)

(58) Field of Classification Search
None
See application file for complete search history.

(56) References Cited

U.S. PATENT DOCUMENTS 7,090,973 B1    8/2006  Breton

FOREIGN PATENT DOCUMENTS

| DK | 200501562 | 11/2005 |
|---|---|---|
| JP | 200433002 | 2/2004 |
| JP | 200650996 | 2/2006 |
| WO | 9606935 | 3/1996 |
| WO | 2009117689 A1 | 9/2009 |

OTHER PUBLICATIONS

Courtin et al, 2002, J Ceral Sci 35 (3), 225-243.
Goldschmid Perlin, 1963, Can J Chem 41 (9), 2272-2277.
Kormelink et al, 1991, Appl Microbiol Technol 35 (6), 753-758.
Sorensen et al., Biotechnology and Bioengineering, vol. 81, No. 6, pp. 726-731 (2003).
Sorensen et al., Enzyme and Microbial Technology, vol. 36, pp. 773-784 (2005).
Nogawa et al., Applied and Environmental Microbiology, vol. 65, No. 9, pp. 3964-3968 (1999).
Van Laere et al., Applied Microbiol Biotechnol, vol. 47, pp. 231-235 (1997).
Sunna et al., Critical Reviews in Biotechnology, vol. 17, No. 1, pp. 39-67 (1997).
Van Den Broek et al., Applied Microbiol Biotechnol, vol. 67, pp. 641-647 (2005).
Ferre et al., European Journal of Biochemistry, vol. 267, pp. 6633-6641 (2000).
International Search Report received in PCT/DK2006/000213.
Adelsberger et al., Microbiology, vol. 150, No. 7, pp. 2257-2266 (2004).
Chica et al., Current Opinion in Biotechnology, vol. 16, No. 4, pp. 378-384 (2005).
Faulds et al., Applied Microbiology and Biotechnology, vol. 60, pp. 489-493 (2002).
Sen et al., Applied Biochemistry and Biotechnology, vol. 143, No. 3, pp. 212-223 (2007).
Sorensen et al., Applied Microbiology and Biotechnology, vol. 73, pp. 850-861 (2006).
Van Laere et al., Applied Microbiology and Biotechnology, vol. 51, No. 5, pp. 606-613 (1999).
Beylot et al., "The Pseudomonas cellulosa glycoside hydrolase family 51 arabinofuranosidase exhibits wide substrate specificity", Biochem. Journal, vol. 358, pp. 607-614 (2001).
Kormelink et al., Carbohydrate Research, vol. 249, pp. 345-353 (1993).

(Continued)

*Primary Examiner* — Hope Robinson
(74) *Attorney, Agent, or Firm* — Robert Starnes

(57) ABSTRACT

The present invention relates to isolated polypeptides having alpha-L-arabinofuranosidase activity and isolated nucleic acid sequences encoding the polypeptides, such that the nucleic acid is operably linked to a heterologous control sequence for expression. The invention also relates to nucleic acid constructs, vectors, and host cells comprising the nucleic acid sequences as well as methods for producing and using the polypeptides set forth in SEQ ID NO: 2 and fragments of SEQ ID NO: 2.

13 Claims, 1 Drawing Sheet

(56) References Cited

OTHER PUBLICATIONS

Pitson et al., FEBS Letters, vol. 398, pp. 7-11 (1996).
Anonymous, Glycoside Hydrolase family classification (2013).
Dalboge, FEMS Microbiology Reviews, vol. 21, pp. 29-42 (1997).
Dervilly-Pinel et al., Carbohydrate Polymers, vol. 55, pp. 171-177 (2004).
Ebbole et al., EMBL Accession No. BU638136 (2003).
Koseki et al., Journal of Bioscience and Bioengineering, vol. 96, No. 3, pp. 232-241 (2003).
Van Den Broek et al., Biotechnology Letters, vol. 21, pp. 441-445 (1999).
Van Den Broek et al., Appl. Microbiol. Biotechnol., vol. 61, No. 1, pp. 55-60 (2003).
Wells, 1990, Biochem 29(37), 8509-8517.
Seffernick et al, 2001, J Bacteriol 183(8), 2405-2410.

```
                        SEQUENCE LISTING

<160> NUMBER OF SEQ ID NOS: 4

<210> SEQ ID NO 1
<211> LENGTH: 1677
<212> TYPE: DNA
<213> ORGANISM: Humicola insolens
<220> FEATURE:
<221> NAME/KEY: CDS
<222> LOCATION: (1)..(1677)
<220> FEATURE:
<221> NAME/KEY: sig_peptide
<222> LOCATION: (1)..(54)

<400> SEQUENCE: 1 atg cta ggc ttg aag gtc ttg tgt ctc tcc gcc gtc gtg ggg acg gcg      48
Met Leu Gly Leu Lys Val Leu Cys Leu Ser Ala Val Val Gly Thr Ala
1               5                   10                  15 gtc tct gtg ccg cac gcg ggc aat ctt ccc cgt cag gcc agc act ttc      96
```

```
                Val Ser Val Pro His Ala Gly Asn Leu Pro Arg Gln Ala Ser Thr Phe
                         20                  25                  30 acc aac ccc gtg ctt tgg gaa gat cac cca gat ctc gaa gtg ttc cgc      144
Thr Asn Pro Val Leu Trp Glu Asp His Pro Asp Leu Glu Val Phe Arg
        35                  40                  45 gtc ggc tca gta ttc tac tac tcc tcg tcc acc ttc gcc tac tcc ccc      192
Val Gly Ser Val Phe Tyr Tyr Ser Ser Ser Thr Phe Ala Tyr Ser Pro
 50                  55                  60 ggc gcg ccc gtc ctc aag tcc tac gac ctc gtc cac tgg acg ccc gtc      240
Gly Ala Pro Val Leu Lys Ser Tyr Asp Leu Val His Trp Thr Pro Val
 65                  70                  75                  80 acc cat tcc gtg ccg cgt ctc aac ttc ggc tcc aac tac gac ctc ccc      288
Thr His Ser Val Pro Arg Leu Asn Phe Gly Ser Asn Tyr Asp Leu Pro
             85                  90                  95 agc ggc acc ccg ggc gcc tac gtc aag ggc atc tgg gcc tca acc ctc      336
Ser Gly Thr Pro Gly Ala Tyr Val Lys Gly Ile Trp Ala Ser Thr Leu
             100                 105                 110 cgc tac cgc cgc tcc aat gac cgc ttc tac tgg tac ggc tgc gtc gaa      384
Arg Tyr Arg Arg Ser Asn Asp Arg Phe Tyr Trp Tyr Gly Cys Val Glu
             115                 120                 125 ggg aga acc tac ctc tgg acc agc ccg ggc ggt aac gcg ctc gcc aac      432
Gly Arg Thr Tyr Leu Trp Thr Ser Pro Gly Gly Asn Ala Leu Ala Asn
 130                 135                 140 aac ggc gag gtg ccc ccc tcg gca tgg aac tgg cag cac acc gcc acc      480
Asn Gly Glu Val Pro Pro Ser Ala Trp Asn Trp Gln His Thr Ala Thr
145                 150                 155                 160 atc gac aac tgc tac tac gac gcc ggc ctg ctc atc gac gac gac gac      528
Ile Asp Asn Cys Tyr Tyr Asp Ala Gly Leu Leu Ile Asp Asp Asp Asp
                 165                 170                 175 acc atg tac atc gcg tac ggc aac ccg acc atc aac gtc gcg cag ctc      576
Thr Met Tyr Ile Ala Tyr Gly Asn Pro Thr Ile Asn Val Ala Gln Leu
                 180                 185                 190 tcc ccc gac ggc acc cgc cag gtg cgc gtg cag cag cgc gtc tac gcg      624
Ser Pro Asp Gly Thr Arg Gln Val Arg Val Gln Gln Arg Val Tyr Ala
             195                 200                 205 cac ccg cag ggc cag acg gtc gag ggc gcg cgc atg tac aag atc cgc      672
His Pro Gln Gly Gln Thr Val Glu Gly Ala Arg Met Tyr Lys Ile Arg
             210                 215                 220 ggc aac tac tac atc ctg gtg acc cgc ccc gcc gac gca gag tac gtg      720
Gly Asn Tyr Tyr Ile Leu Val Thr Arg Pro Ala Asp Ala Glu Tyr Val
225                 230                 235                 240 ctg cgg tcg acg acg ggg tcg ccg ttc ggc ccg tac gag gcg cgc acg      768
Leu Arg Ser Thr Thr Gly Ser Pro Phe Gly Pro Tyr Glu Ala Arg Thr
                 245                 250                 255 ctg gtg tcg cgg atc cag ggc ccg ctg gcc aac gcc ggg ttc gcg cac      816
Leu Val Ser Arg Ile Gln Gly Pro Leu Ala Asn Ala Gly Phe Ala His
                 260                 265                 270 cag ggc ggc atc gtc gac gcg ccg gat ggg acg tgg cac tac gtc gcg      864
Gln Gly Gly Ile Val Asp Ala Pro Asp Gly Thr Trp His Tyr Val Ala
             275                 280                 285 ttc atg gat gcg tat ccc ggc gga cgc atc ccc gtg gtg gcg ccg ctg      912
Phe Met Asp Ala Tyr Pro Gly Gly Arg Ile Pro Val Val Ala Pro Leu
             290                 295                 300 cgg tgg acg gcg gat ggg tgg ccc gag gtg gtc acg gat tcg caa ggg      960
Arg Trp Thr Ala Asp Gly Trp Pro Glu Val Val Thr Asp Ser Gln Gly
305                 310                 315                 320 agg tgg ggg acg agc tat ccc att cca gtt cgc gga gca aag aac gcg     1008
Arg Trp Gly Thr Ser Tyr Pro Ile Pro Val Arg Gly Ala Lys Asn Ala
                 325                 330                 335
```

| | | | | | | | | | | | | | | | | |
|---|---|---|---|---|---|---|---|---|---|---|---|---|---|---|---|---|
| acg | gag | ggg | ctg | gcg | agc | acg | gat | ctg | gac | gag | ttc | cgc | ggg | acg | agg | 1056 |
| Thr | Glu | Gly | Leu | Ala | Ser | Thr | Asp | Leu | Asp | Glu | Phe | Arg | Gly | Thr | Arg | |
| | | | 340 | | | | | 345 | | | | | 350 | | | |
| ttc | agc | gag | cat | tgg | gag | tgg | aat | cat | aac | ccg | gac | acg | agc | aag | ttt | 1104 |
| Phe | Ser | Glu | His | Trp | Glu | Trp | Asn | His | Asn | Pro | Asp | Thr | Ser | Lys | Phe | |
| | | 355 | | | | | 360 | | | | | 365 | | | | |
| acg | ttg | ctg | ggc | ggt | aac | gag | ggc | ggg | ctc | atc | ctc | cgg | aca | gcg | acc | 1152 |
| Thr | Leu | Leu | Gly | Gly | Asn | Glu | Gly | Gly | Leu | Ile | Leu | Arg | Thr | Ala | Thr | |
| 370 | | | | | 375 | | | | | 380 | | | | | | |
| gtg | acg | ggg | gat | ttg | ttt | gcc | gca | agg | aat | acg | ctc | acg | agg | agg | atc | 1200 |
| Val | Thr | Gly | Asp | Leu | Phe | Ala | Ala | Arg | Asn | Thr | Leu | Thr | Arg | Arg | Ile | |
| 385 | | | | | 390 | | | | | 395 | | | | | 400 | |
| gcg | gga | ccc | aag | gcc | agt | gga | atc | ttc | cgg | ctg | gat | gtg | cgc | ggg | atg | 1248 |
| Ala | Gly | Pro | Lys | Ala | Ser | Gly | Ile | Phe | Arg | Leu | Asp | Val | Arg | Gly | Met | |
| | | | | 405 | | | | | 410 | | | | | 415 | | |
| cgc | gac | ggt | gac | cgg | gcc | ggc | gcc | gtg | ctg | ttc | cgg | gat | cgt | gcg | gcg | 1296 |
| Arg | Asp | Gly | Asp | Arg | Ala | Gly | Ala | Val | Leu | Phe | Arg | Asp | Arg | Ala | Ala | |
| | | | 420 | | | | | 425 | | | | | 430 | | | |
| tac | atc | ggg | gtg | tgg | aag | cag | ggc | aac | gag | gcg | cgg | att | gtc | atg | gtg | 1344 |
| Tyr | Ile | Gly | Val | Trp | Lys | Gln | Gly | Asn | Glu | Ala | Arg | Ile | Val | Met | Val | |
| | | | 435 | | | | | 440 | | | | | 445 | | | |
| gac | gac | ctg | cgg | ttg | aac | gag | gat | ggt | tgg | agg | acg | gcg | tcc | acc | ggc | 1392 |
| Asp | Asp | Leu | Arg | Leu | Asn | Glu | Asp | Gly | Trp | Arg | Thr | Ala | Ser | Thr | Gly | |
| 450 | | | | | 455 | | | | | 460 | | | | | | |
| aga | gtg | gcc | gcc | aac | ggt | ccg | gtg | atc | gac | acg | aac | gct | cag | cag | gat | 1440 |
| Arg | Val | Ala | Ala | Asn | Gly | Pro | Val | Ile | Asp | Thr | Asn | Ala | Gln | Gln | Asp | |
| 465 | | | | | 470 | | | | | 475 | | | | | 480 | |
| atc | tgg | ctg | cga | att | gat | gcg | gac | atc | aca | ccg | gcg | ttt | ggg | acg | aac | 1488 |
| Ile | Trp | Leu | Arg | Ile | Asp | Ala | Asp | Ile | Thr | Pro | Ala | Phe | Gly | Thr | Asn | |
| | | | | 485 | | | | | 490 | | | | | 495 | | |
| acg | gag | cgc | acg | acg | acg | ttc | tac | tac | agt | att | gat | ggt | ggg | agg | acg | 1536 |
| Thr | Glu | Arg | Thr | Thr | Thr | Phe | Tyr | Tyr | Ser | Ile | Asp | Gly | Gly | Arg | Thr | |
| | | | 500 | | | | | 505 | | | | | 510 | | | |
| tat | acc | agg | ctg | ggc | cct | gcc | ttt | gcg | atg | acc | aat | tct | tgg | aga | tac | 1584 |
| Tyr | Thr | Arg | Leu | Gly | Pro | Ala | Phe | Ala | Met | Thr | Asn | Ser | Trp | Arg | Tyr | |
| | | 515 | | | | | 520 | | | | | 525 | | | | |
| ttc | acc | gga | tac | cgg | ttt | gga | gtg | ttc | aac | ttt | tcg | acc | aag | agt | ctt | 1632 |
| Phe | Thr | Gly | Tyr | Arg | Phe | Gly | Val | Phe | Asn | Phe | Ser | Thr | Lys | Ser | Leu | |
| | 530 | | | | | 535 | | | | | 540 | | | | | |
| gga | ggt | gag | gtg | aag | gtt | aag | ggg | ttc | aag | atg | aac | atg | atc | tag | | 1677 |
| Gly | Gly | Glu | Val | Lys | Val | Lys | Gly | Phe | Lys | Met | Asn | Met | Ile | | | |
| 545 | | | | | 550 | | | | | 555 | | | | | | |

<210> SEQ ID NO 2
<211> LENGTH: 558
<212> TYPE: PRT
<213> ORGANISM: Humicola insolens

<400> SEQUENCE: 2

Met Leu Gly Leu Lys Val Leu Cys Leu Ser Ala Val Val Gly Thr Ala
1               5                   10                  15

Val Ser Val Pro His Ala Gly Asn Leu Pro Arg Gln Ala Ser Thr Phe
            20                  25                  30

Thr Asn Pro Val Leu Trp Glu Asp His Pro Asp Leu Glu Val Phe Arg
        35                  40                  45

Val Gly Ser Val Phe Tyr Tyr Ser Ser Thr Phe Ala Tyr Ser Pro
    50                  55                  60

Gly Ala Pro Val Leu Lys Ser Tyr Asp Leu Val His Trp Thr Pro Val
65                  70                  75                  80

-continued

```
Thr His Ser Val Pro Arg Leu Asn Phe Gly Ser Asn Tyr Asp Leu Pro
             85                  90                  95

Ser Gly Thr Pro Gly Ala Tyr Val Lys Gly Ile Trp Ala Ser Thr Leu
            100                 105                 110

Arg Tyr Arg Arg Ser Asn Asp Arg Phe Tyr Trp Tyr Gly Cys Val Glu
            115                 120                 125

Gly Arg Thr Tyr Leu Trp Thr Ser Pro Gly Gly Asn Ala Leu Ala Asn
            130                 135                 140

Asn Gly Glu Val Pro Pro Ser Ala Trp Asn Gln His Thr Ala Thr
145                 150                 155                 160

Ile Asp Asn Cys Tyr Tyr Asp Ala Gly Leu Leu Ile Asp Asp Asp
                165                 170                 175

Thr Met Tyr Ile Ala Tyr Gly Asn Pro Thr Ile Asn Val Ala Gln Leu
            180                 185                 190

Ser Pro Asp Gly Thr Arg Gln Val Arg Val Gln Gln Arg Val Tyr Ala
            195                 200                 205

His Pro Gln Gly Gln Thr Val Glu Gly Ala Arg Met Tyr Lys Ile Arg
            210                 215                 220

Gly Asn Tyr Tyr Ile Leu Val Thr Arg Pro Ala Asp Ala Glu Tyr Val
225                 230                 235                 240

Leu Arg Ser Thr Thr Gly Ser Pro Phe Gly Pro Tyr Glu Ala Arg Thr
                245                 250                 255

Leu Val Ser Arg Ile Gln Gly Pro Leu Ala Asn Ala Gly Phe Ala His
                260                 265                 270

Gln Gly Gly Ile Val Asp Ala Pro Asp Gly Thr Trp His Tyr Val Ala
            275                 280                 285

Phe Met Asp Ala Tyr Pro Gly Gly Arg Ile Pro Val Val Ala Pro Leu
            290                 295                 300

Arg Trp Thr Ala Asp Gly Trp Pro Glu Val Val Thr Asp Ser Gln Gly
305                 310                 315                 320

Arg Trp Gly Thr Ser Tyr Pro Ile Pro Val Arg Gly Ala Lys Asn Ala
                325                 330                 335

Thr Glu Gly Leu Ala Ser Thr Asp Leu Asp Glu Phe Arg Gly Thr Arg
            340                 345                 350

Phe Ser Glu His Trp Glu Trp Asn His Asn Pro Asp Thr Ser Lys Phe
            355                 360                 365

Thr Leu Leu Gly Gly Asn Glu Gly Gly Leu Ile Leu Arg Thr Ala Thr
            370                 375                 380

Val Thr Gly Asp Leu Phe Ala Ala Arg Asn Thr Leu Thr Arg Arg Ile
385                 390                 395                 400

Ala Gly Pro Lys Ala Ser Gly Ile Phe Arg Leu Asp Val Arg Gly Met
                405                 410                 415

Arg Asp Gly Asp Arg Ala Gly Ala Val Leu Phe Arg Asp Arg Ala Ala
            420                 425                 430

Tyr Ile Gly Val Trp Lys Gln Gly Asn Glu Ala Arg Ile Val Met Val
            435                 440                 445

Asp Asp Leu Arg Leu Asn Glu Asp Gly Trp Arg Thr Ala Ser Thr Gly
            450                 455                 460

Arg Val Ala Ala Asn Gly Pro Val Ile Asp Thr Asn Ala Gln Gln Asp
465                 470                 475                 480

Ile Trp Leu Arg Ile Asp Ala Asp Ile Thr Pro Ala Phe Gly Thr Asn
                485                 490                 495

Thr Glu Arg Thr Thr Thr Phe Tyr Tyr Ser Ile Asp Gly Gly Arg Thr
```

```
                500               505                 510
Tyr Thr Arg Leu Gly Pro Ala Phe Ala Met Thr Asn Ser Trp Arg Tyr
            515                 520                 525

Phe Thr Gly Tyr Arg Phe Gly Val Phe Asn Phe Ser Thr Lys Ser Leu
            530                 535                 540

Gly Gly Glu Val Lys Val Lys Gly Phe Lys Met Asn Met Ile
545                 550                 555

<210> SEQ ID NO 3
<211> LENGTH: 2200
<212> TYPE: DNA
<213> ORGANISM: Miripilus giganteus
<220> FEATURE:
<221> NAME/KEY: CDS
<222> LOCATION: (46)..(1974)
<220> FEATURE:
<221> NAME/KEY: sig_peptide
<222> LOCATION: (46)..(94)

<400> SEQUENCE: 3
actagtaacg gccgccagtg tgctggaaag ggctcgctcg acacg atg aag ctg ctt      57
                                                Met Lys Leu Leu
                                                 1 ttc ttg ctc ggg gcc ttc gtt gcg caa tgt ctc gcg gtc aca gtg acc      105
Phe Leu Leu Gly Ala Phe Val Ala Gln Cys Leu Ala Val Thr Val Thr
5                   10                  15                  20 gtt aac aag aac cct agt cac acg gta ccg tcc acg ctc tat ggc ctg      153
Val Asn Lys Asn Pro Ser His Thr Val Pro Ser Thr Leu Tyr Gly Leu
                25                  30                  35 atg ttt gag gac atc aac cat agc ggt gat ggc ctg tac gcg gag          201
Met Phe Glu Asp Ile Asn His Ser Gly Asp Gly Leu Tyr Ala Glu
            40                  45                  50 ttg ttg caa aac agg gct ttc caa cag gtt acc ccg aac acg gcc gct      249
Leu Leu Gln Asn Arg Ala Phe Gln Gln Val Thr Pro Asn Thr Ala Ala
        55                  60                  65 gca ctc gct gca tgg cat ccc atc agc aat gcg aag ctg gcc gta ata      297
Ala Leu Ala Ala Trp His Pro Ile Ser Asn Ala Lys Leu Ala Val Ile
    70                  75                  80 caa gac cca tct cct gtc tcc aat gca ttg ccg aat tcc ctt caa ttc      345
Gln Asp Pro Ser Pro Val Ser Asn Ala Leu Pro Asn Ser Leu Gln Phe
85                  90                  95                  100 tcc gtg ccc agt gga tcg agc ggc agg gtc ggc ttt acc aac gag ggt      393
Ser Val Pro Ser Gly Ser Ser Gly Arg Val Gly Phe Thr Asn Glu Gly
                105                 110                 115 ttc tgg gga atc aaa gtc gat tcc act tgg acg tac aaa gcc tcg ctc      441
Phe Trp Gly Ile Lys Val Asp Ser Thr Trp Thr Tyr Lys Ala Ser Leu
            120                 125                 130 ttc ttc cgc ttc ccc aca tcg tcg tcc ttc tcg gga gcg ctc acc gtt      489
Phe Phe Arg Phe Pro Thr Ser Ser Ser Phe Ser Gly Ala Leu Thr Val
        135                 140                 145 ggg ctg cag acg aac gcc ggg aga gtg ctg gca cag aac tcc acg cag      537
Gly Leu Gln Thr Asn Ala Gly Arg Val Leu Ala Gln Asn Ser Thr Gln
    150                 155                 160 atc cgc ggg acg acc acg aag tgg acg cag atc aac ctg gag ctc cac      585
Ile Arg Gly Thr Thr Thr Lys Trp Thr Gln Ile Asn Leu Glu Leu His
165                 170                 175                 180 cct acc gcc tct gcc ccc gac gtc agc aac agc ttc ttt gtc acg att      633
Pro Thr Ala Ser Ala Pro Asp Val Ser Asn Ser Phe Phe Val Thr Ile
                185                 190                 195 gac ggg gcc gct ggc gcc ggt cag acg atc aac ttc gcc atg ttc tcg      681
Asp Gly Ala Ala Gly Ala Gly Gln Thr Ile Asn Phe Ala Met Phe Ser
```

-continued

| | | |
|---|---|---|
| ctc ttc cct ccc acg ttc aag aac agg ccg aat ggg ctg cgc gct gac<br>Leu Phe Pro Pro Thr Phe Lys Asn Arg Pro Asn Gly Leu Arg Ala Asp<br>215                   220                   225 | 729 |
| atc gcc gag act ctg gcc gag atg ggc ccg tcc ttt ttc cgc ttc cca<br>Ile Ala Glu Thr Leu Ala Glu Met Gly Pro Ser Phe Phe Arg Phe Pro<br>230                     235                   240 | 777 |
| ggt ggg aac aac ctg gag ggc caa acg acg gcg acg agg tgg cag tgg<br>Gly Gly Asn Asn Leu Glu Gly Gln Thr Thr Ala Thr Arg Trp Gln Trp<br>245                     250                   255                   260 | 825 |
| aat gct acc gtc ggc tcg ctg ctg gac cgc ccc ggc cgg gtg ggc gac<br>Asn Ala Thr Val Gly Ser Leu Leu Asp Arg Pro Gly Arg Val Gly Asp<br>                   265                   270                   275 | 873 |
| tgg gga tac gtg aac acg gac ggt cta ggt ctt ctg gag tat ctc cag<br>Trp Gly Tyr Val Asn Thr Asp Gly Leu Gly Leu Leu Glu Tyr Leu Gln<br>                   280                   285                   290 | 921 |
| ttc ttc gaa gat acg ggc atg gag ccg atc atg gcg gtc tgg gca ggc<br>Phe Phe Glu Asp Thr Gly Met Glu Pro Ile Met Ala Val Trp Ala Gly<br>               295                   300                   305 | 969 |
| tat tct ctc ggc ggc aca agc ctt gct gag aac cag ctc gca ccg tac<br>Tyr Ser Leu Gly Gly Thr Ser Leu Ala Glu Asn Gln Leu Ala Pro Tyr<br>310                   315                   320 | 1017 |
| ata cag caa gcg ata gat cag att aac ttt gtc atc ggg gac cct gca<br>Ile Gln Gln Ala Ile Asp Gln Ile Asn Phe Val Ile Gly Asp Pro Ala<br>325                   330                   335                   340 | 1065 |
| aag agt gca cct gcg gcg ctc cgt gct tcc ctg ggc cac cca gag ccc<br>Lys Ser Ala Pro Ala Ala Leu Arg Ala Ser Leu Gly His Pro Glu Pro<br>                   345                   350                   355 | 1113 |
| ttc acg ctc cgc ttc gtg gaa gtg gga aac gag gac ttc ttc gcg gcg<br>Phe Thr Leu Arg Phe Val Glu Val Gly Asn Glu Asp Phe Phe Ala Ala<br>                   360                   365                   370 | 1161 |
| ggc tcg tac cca tac cgc tgg cac gac ttc gtt acc gca ctt cag gcg<br>Gly Ser Tyr Pro Tyr Arg Trp His Asp Phe Val Thr Ala Leu Gln Ala<br>                   375                   380                   385 | 1209 |
| caa ttc ccc cag atc aga ttc atc gcg acc acc aac gcc tgg aac ccg<br>Gln Phe Pro Gln Ile Arg Phe Ile Ala Thr Thr Asn Ala Trp Asn Pro<br>390                   395                   400 | 1257 |
| gtt ctg tcc ccc gtc ccg cag tcg tat gat gta cac gtc tat cag aca<br>Val Leu Ser Pro Val Pro Gln Ser Tyr Asp Val His Val Tyr Gln Thr<br>405                   410                   415                   420 | 1305 |
| ccg acc tgg ttc tac caa aat gct ttc tac tac gac ggc ttc cag cgc<br>Pro Thr Trp Phe Tyr Gln Asn Ala Phe Tyr Tyr Asp Gly Phe Gln Arg<br>                   425                   430                   435 | 1353 |
| aac ggc acc aca tac ttt gag ggg gag tac gcc gcc atc tcc acc aac<br>Asn Gly Thr Thr Tyr Phe Glu Gly Glu Tyr Ala Ala Ile Ser Thr Asn<br>                   440                   445                   450 | 1401 |
| gcg aac gat ttg ttc ggt act gtt gcc gac ggt cgc ttg gcg ttc cct<br>Ala Asn Asp Leu Phe Gly Thr Val Ala Asp Gly Arg Leu Ala Phe Pro<br>                   455                   460                   465 | 1449 |
| aca gtg caa agt gct acc ggg gag gcc gca ttc atg acc ggc ttg gag<br>Thr Val Gln Ser Ala Thr Gly Glu Ala Ala Phe Met Thr Gly Leu Glu<br>470                   475                   480 | 1497 |
| cgc aac agc gac atc gtc ttc gcc gcg tcc tac gca cct ctg ctg cag<br>Arg Asn Ser Asp Ile Val Phe Ala Ala Ser Tyr Ala Pro Leu Leu Gln<br>485                   490                   495                   500 | 1545 |
| cac gtc aac tcc act caa tgg acc ccc gac ctg gtt tcc tac gac gcc<br>His Val Asn Ser Thr Gln Trp Thr Pro Asp Leu Val Ser Tyr Asp Ala<br>                   505                   510                   515 | 1593 |
| ggc tcc gtt att aag tcg acg agc ttc ttc gcc cag aag ctg ttc gcc | 1641 |

```
Gly Ser Val Ile Lys Ser Thr Ser Phe Phe Ala Gln Lys Leu Phe Ala
            520                 525                 530 ttg aac aag ggc gac caa tac ctc ccg agc acg ctc ccg acc aac ggt      1689
Leu Asn Lys Gly Asp Gln Tyr Leu Pro Ser Thr Leu Pro Thr Asn Gly
        535                 540                 545 ggc acg ctg cac tgg agc atc act cgg gcc tct agc tcc ggc aag acg      1737
Gly Thr Leu His Trp Ser Ile Thr Arg Ala Ser Ser Ser Gly Lys Thr
    550                 555                 560 ttc atc aag atc gcg aac gcc ggc agc tca gcg cag agc ctc acc ttc      1785
Phe Ile Lys Ile Ala Asn Ala Gly Ser Ser Ala Gln Ser Leu Thr Phe
565                 570                 575                 580 cag ctg acc cag ttc aac tcg gtc tcc agc acc gga acg ctc cag gtc      1833
Gln Leu Thr Gln Phe Asn Ser Val Ser Ser Thr Gly Thr Leu Gln Val
            585                 590                 595 ctc acc gga ccg gag acc gcc agc aac acg cct gag gcg ccg cag gcc      1881
Leu Thr Gly Pro Glu Thr Ala Ser Asn Thr Pro Glu Ala Pro Gln Ala
        600                 605                 610 atc gtt ccc aag acg agc acg atc ggc acc ggc aag act ttc acg tac      1929
Ile Val Pro Lys Thr Ser Thr Ile Gly Thr Gly Lys Thr Phe Thr Tyr
    615                 620                 625 aac gct ccc gca ttc agc gtc agt gtc atc acc gtc acc acg aac          1974
Asn Ala Pro Ala Phe Ser Val Ser Val Ile Thr Val Thr Thr Asn
630                 635                 640 tgaacgaaga agcacaacgc agcacgagga ccagaggacg gcgcggatgc gagactgccg    2034
agataccatt gccgcgaagg ggtgcagtgg tgccgtaact cgcaagggggg aacgggatcg   2094 tccgaatcgg atgggtgtgg attaggttgc gtcttcactg tttactaggc ggtgtatgcg   2154
agcgtagcta gtgcggtcct attgtaattt tgtgaggtct atctcc                  2200

<210> SEQ ID NO 4
<211> LENGTH: 643
<212> TYPE: PRT
<213> ORGANISM: Miripilus giganteus

<400> SEQUENCE: 4

Met Lys Leu Leu Phe Leu Leu Gly Ala Phe Val Ala Gln Cys Leu Ala
1               5                   10                  15

Val Thr Val Thr Val Asn Lys Asn Pro Ser His Thr Val Pro Ser Thr
            20                  25                  30

Leu Tyr Gly Leu Met Phe Glu Asp Ile Asn His Ser Gly Asp Gly Gly
        35                  40                  45

Leu Tyr Ala Glu Leu Leu Gln Asn Arg Ala Phe Gln Gln Val Thr Pro
    50                  55                  60

Asn Thr Ala Ala Ala Leu Ala Ala Trp His Pro Ile Ser Asn Ala Lys
65                  70                  75                  80

Leu Ala Val Ile Gln Asp Pro Ser Pro Val Ser Asn Ala Leu Pro Asn
                85                  90                  95

Ser Leu Gln Phe Ser Val Pro Ser Gly Ser Ser Arg Val Gly Phe
            100                 105                 110

Thr Asn Glu Gly Phe Trp Gly Ile Lys Val Asp Ser Thr Trp Thr Tyr
        115                 120                 125

Lys Ala Ser Leu Phe Phe Arg Phe Pro Thr Ser Ser Phe Ser Gly
    130                 135                 140

Ala Leu Thr Val Gly Leu Gln Thr Asn Ala Gly Arg Val Leu Ala Gln
145                 150                 155                 160

Asn Ser Thr Gln Ile Arg Gly Thr Thr Thr Lys Trp Thr Gln Ile Asn
                165                 170                 175
```

```
Leu Glu Leu His Pro Thr Ala Ser Ala Pro Asp Val Ser Asn Ser Phe
            180                 185                 190
Phe Val Thr Ile Asp Gly Ala Ala Gly Ala Gly Gln Thr Ile Asn Phe
        195                 200                 205
Ala Met Phe Ser Leu Phe Pro Pro Thr Phe Lys Asn Arg Pro Asn Gly
    210                 215                 220
Leu Arg Ala Asp Ile Ala Glu Thr Leu Ala Glu Met Gly Pro Ser Phe
225                 230                 235                 240
Phe Arg Phe Pro Gly Gly Asn Asn Leu Glu Gly Gln Thr Thr Ala Thr
                245                 250                 255
Arg Trp Gln Trp Asn Ala Thr Val Gly Ser Leu Leu Asp Arg Pro Gly
            260                 265                 270
Arg Val Gly Asp Trp Gly Tyr Val Asn Thr Asp Gly Leu Gly Leu Leu
        275                 280                 285
Glu Tyr Leu Gln Phe Phe Glu Asp Thr Gly Met Glu Pro Ile Met Ala
    290                 295                 300
Val Trp Ala Gly Tyr Ser Leu Gly Gly Thr Ser Leu Ala Glu Asn Gln
305                 310                 315                 320
Leu Ala Pro Tyr Ile Gln Gln Ala Ile Asp Gln Ile Asn Phe Val Ile
                325                 330                 335
Gly Asp Pro Ala Lys Ser Ala Pro Ala Ala Leu Arg Ala Ser Leu Gly
            340                 345                 350
His Pro Glu Pro Phe Thr Leu Arg Phe Val Glu Val Gly Asn Glu Asp
        355                 360                 365
Phe Phe Ala Ala Gly Ser Tyr Pro Tyr Arg Trp His Asp Phe Val Thr
    370                 375                 380
Ala Leu Gln Ala Gln Phe Pro Gln Ile Arg Phe Ile Ala Thr Thr Asn
385                 390                 395                 400
Ala Trp Asn Pro Val Leu Ser Pro Val Pro Gln Ser Tyr Asp Val His
                405                 410                 415
Val Tyr Gln Thr Pro Thr Trp Phe Tyr Gln Asn Ala Phe Tyr Tyr Asp
            420                 425                 430
Gly Phe Gln Arg Asn Gly Thr Thr Tyr Phe Glu Gly Glu Tyr Ala Ala
        435                 440                 445
Ile Ser Thr Asn Ala Asn Asp Leu Phe Gly Thr Val Ala Asp Gly Arg
    450                 455                 460
Leu Ala Phe Pro Thr Val Gln Ser Ala Thr Gly Glu Ala Ala Phe Met
465                 470                 475                 480
Thr Gly Leu Glu Arg Asn Ser Asp Ile Val Phe Ala Ala Ser Tyr Ala
                485                 490                 495
Pro Leu Leu Gln His Val Asn Ser Thr Gln Trp Thr Pro Asp Leu Val
            500                 505                 510
Ser Tyr Asp Ala Gly Ser Val Ile Lys Ser Thr Ser Phe Phe Ala Gln
        515                 520                 525
Lys Leu Phe Ala Leu Asn Lys Gly Asp Gln Tyr Leu Pro Ser Thr Leu
    530                 535                 540
Pro Thr Asn Gly Gly Thr Leu His Trp Ser Ile Thr Arg Ala Ser Ser
545                 550                 555                 560
Ser Gly Lys Thr Phe Ile Lys Ile Ala Asn Ala Gly Ser Ser Ala Gln
                565                 570                 575
Ser Leu Thr Phe Gln Leu Thr Gln Phe Asn Ser Val Ser Ser Thr Gly
            580                 585                 590
```

```
Thr Leu Gln Val Leu Thr Gly Pro Glu Thr Ala Ser Asn Thr Pro Glu
        595                 600                 605

Ala Pro Gln Ala Ile Val Pro Lys Thr Ser Thr Ile Gly Thr Gly Lys
        610                 615                 620

Thr Phe Thr Tyr Asn Ala Pro Ala Phe Ser Val Ser Val Ile Thr Val
625                 630                 635                 640

Thr Thr Asn
```

NUCLEIC ACID CONSTRUCT WITH GENE ENCODING AN ARABINOFURANOSIDASE POLYPEPTIDE AND METHODS OF USING SAME

CROSS-REFERENCE TO RELATED APPLICATIONS

This application is a divisional application of U.S. application Ser. No. 11/911,683 filed Oct. 16, 2007, now abandoned, which is a 35 U.S.C. §371 national application of PCT/DK2006/000213 filed Apr. 25, 2006, which claims priority or the benefit under 35 U.S.C. §119 of Danish application nos. PA 2005 00609 and PA 2005 01562 filed Apr. 26, 2005 and Nov. 10, 2005, respectively, and U.S. Provisional Application Nos. 60/676,115 and 60/735,661 filed Apr. 29, 2005 and Nov. 10, 2005, respectively, the contents of which are fully incorporated herein by reference.

FIELD OF THE INVENTION

The present invention relates to isolated polypeptides having alpha-L-arabinofuranosidase activity and isolated nucleic acid sequences encoding the polypeptides. The invention also relates to nucleic acid constructs, vectors, and host cells comprising the nucleic acid sequences as well as methods for producing and using the polypeptides.

BACKGROUND OF THE INVENTION

Arabinofuranosidases are capable of hydrolyzing terminal non-reducing alpha-L-arabinofuranoside residues in alpha-L-arabinosides and are classified as EC 3.2.1.55. Arabinofuranosidases have been isolated from several organisms including filamentous fungi. However, very few alpha-arabinofuranosidases able to liberate arabinose from di-substituted xyloses are known. From *Bifidobacterium adolescentis* an intracellular enzyme able to release arabinose from C3 of di-substituted xylose (also internally) has been described (Van Laere, 1997, Appl. Microbiol. Biotechnol, 47, 231-235 and Van den Broek, 2005, Applied Microbiology and Biotechnology). From barley an enzyme active on mono- and terminally di-substituted xyloses has been isolated, but it has little activity on internally di-substituted xyloses (Ferre, 2000, Eur. J. Biochem., 267, 6633-6641). An enzyme from *Trichoderma reesei* is possibly active on terminally di-substituted residues (activity seen on 3,5-di-O-alpha-Larabinofuranosyl-alpha-L-arabinofuranoside), but has no activity towards an oligo-substrate with internally C3 substituted arabinose (Nogawa, 1999, Appl. Environ. Microbiol., 65, 3964-3968).

A comparison with full-length prior-art sequences shows that the mature amino acid sequence shown in SEQ ID NO:2 has 72% homology with an amino acid sequence from *Chaetomium globosum*, and the corresponding DNA sequence in SEQ ID NO:1 shows 73% homology with that of the corresponding *Chaetomium globosum* DNA sequence. The homology between the sequence shown in SEQ ID NO:2 and the bacterial GH43 alpha-L-arabinofuranosidase from *Bifidobacterium* sp. is 25%. The mature amino acid sequence shown in SEQ ID NO:4 has 38% homology with the arabinofuranosidase from *Aspergillus niger*.

SUMMARY OF THE INVENTION

The inventors have isolated alpha-L-arabinofuranosidases from strains of the filamentous fungi *Humicola insolens* (SEQ ID NO:2) and *Meripilus giganteus* (SEQ ID NO:4). The inventors also isolated the genes encoding the novel alpha-L-arabinofuranosidases. The enzymes are extracellular. The alpha-L-arabinofuranosidases from *Humicola insolens* belongs to GH43 and the alpha-L-arabinofuranosidases from *Meripilus giganteus* belongs to GH51.

The alpha-L-arabinofuranosidase from *Humicola insolens* is able to liberate arabinose from di-substituted xyloses, i.e. the alpha-L-arabinofuranosidase is active on xylose units of wheat arabinoxylan with arabinose attached to C2 and C3. The activity towards di-substituted xyloses is essential for total hydrolysis of arabinoxylan to monosaccharides e.g. in production of ethanol from biomass.

Accordingly, in a first aspect the invention provides an arabinofuranosidase derived from a fungus, preferably a species within *Humicola*, said arabinofuranosidase capable of releasing arabinose from di-substitued xyloses.

Accordingly, in a second aspect the invention provides an arabinofuranosidase which is: a) a polypeptide having an amino acid sequence as the mature peptide shown in SEQ ID NO: 2, or which can be obtained there from by substitution, deletion, and/or insertion of one or more amino acids; b) an analogue of the polypeptide defined in (i) or (i) which: i) has at least 80% homology with said polypeptide, ii) is an allelic variant of said polypeptide, c) a polypeptide which is encoded by a nucleic acid sequence which hybridizes under high stringency conditions with a complementary strand of the nucleic acid sequence of SEQ ID NO:2 encoding the mature polypeptide or a subsequence thereof having at least 100 nucleotides.

Accordingly, in a third aspect the invention provides an arabinofuranosidase which is: a) a polypeptide having an amino acid sequence as the mature peptide shown in SEQ ID NO: 4, or which can be obtained there from by substitution, deletion, and/or insertion of one or more amino acids; b) an analogue of the polypeptide defined in (i) or (ii) which: i) has at least 60% homology with said polypeptide, ii) is an allelic variant of said polypeptide, c) a polypeptide which is encoded by a nucleic acid sequence which hybridizes under high stringency conditions with a complementary strand of the nucleic acid sequence of SEQ ID NO:4 encoding the mature polypeptide or a subsequence thereof having at least 100 nucleotides.

In a fourth aspect the invention provides a nucleic acid sequence comprising a nucleic acid sequence which encodes the arabinofuranosidase of the first or second aspect.

In a fifth aspect the invention provides a nucleic acid sequence which comprises: a) the DNA sequence encoding any of the arabinofuranosidases shown in SEQ ID NO:2 and SEQ ID NO:4, b) an analog DNA sequence which i) has at least 80% homology with any of said DNA sequences, or ii) hybridizes at high stringency with a complementary strand of any of said DNA sequences or a subsequence thereof having at least 100 nucleotides, iii) is an allelic variant thereof, or c) a complementary strand to a) or b).

In a sixth aspect the invention provides a nucleic acid sequence which has at least 80% homology with any of the DNA sequences shown in SEQ ID NO:1 and SEQ ID NO:3, or a) hybridizes at high stringency with a complementary strand of any of said DNA sequences or a subsequence thereof having at least 100 nucleotides, b) is an allelic variant thereof, or c) a complementary strand to a) or b).

In a seventh aspect the invention provides a nucleic acid construct comprising the nucleic acid sequence of the second, third and fourth aspect operably linked to one or more control sequences capable of directing the expression of the arabinofuranosidase in a suitable expression host.

In an eighth aspect the invention provides a recombinant expression vector comprising the nucleic acid construct of the seventh aspect.

In a ninth aspect the invention provides a recombinant host cell comprising the nucleic acid construct of the sixth aspect.

In a tenth aspect the invention provides a method for producing an arabinofuranosidase comprising cultivating the host cell of the ninth aspect under conditions conducive to production of the arabinofuranosidase, and recovering the arabinofuranosidase.

In an eleventh aspect the invention provides a composition comprising the arabinofuranosidase of the first and second aspect.

In further aspects the invention provides uses of the arabinofuranosidases of the first and second aspect.

BRIEF DESCRIPTION OF THE DRAWING

FIG. 1A shows intact arabinoxylan.
FIG. 1B shows di-substituted arabinoxylan.
FIG. 1C shows singly substituted arabinoxylan.
FIG. 2 A-C show arabinoxylo-oligosaccharides

DETAILED DESCRIPTION OF THE INVENTION

Figure 1A:
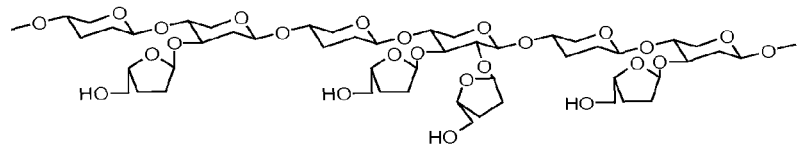
FIG. 1A-C show arabinoxylan polymers
Figure 1B:
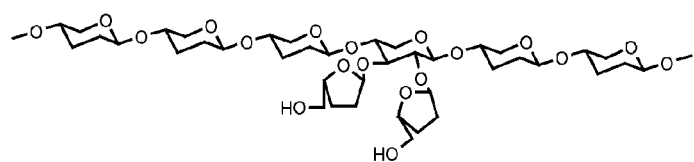
Figure 1C:
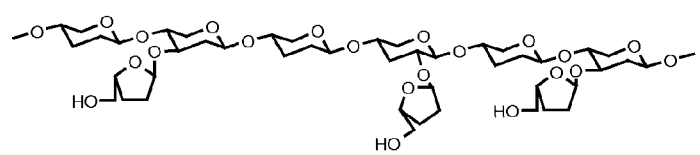
Figure 2A:
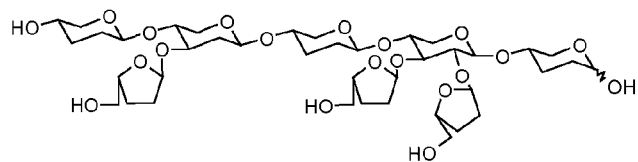
FIG. 2A shows arabinosyl groups linked to internal C-3
Figure 2B:
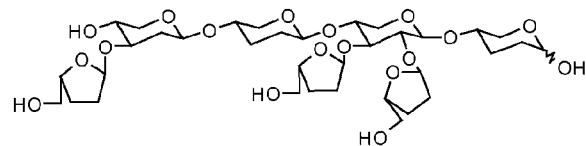
FIG. 2B shows arabinosyl groups linked to terminal C-3
Figure 2C:
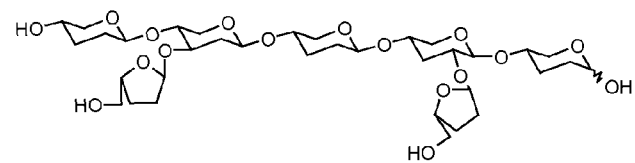
FIG. 2C shows arabinosyl groups linked to internal C-2

In a embodiment of the second aspect of the present invention, the isolated polypeptide has an amino acid sequence which has at least 80% identity with the amino acid sequence shown as amino acids 1 to 558 of SEQ ID NO:2. In an interesting embodiment of the invention the polypeptide has at least 75%, at least 85%, at least 90%, at least 95%, at least 96%, at least 97%, at least 98%, or at least 99% identity with the amino acid sequence shown as amino acids 1 to 558 of SEQ ID NO:2.

In an embodiment of the third aspect of the present invention, the isolated polypeptide has an amino acid sequence which has at least 50% identity with the amino acid sequence shown as amino acids 1 to 643 of SEQ ID NO:4. In an interesting embodiment of the invention the polypeptide has at least 60%, at least 70%, at least 80% at least 85%, at least 90%, at least 95%, at least 96%, at least 97%, at least 98%, or at least 99% identity with the amino acid sequence shown as amino acids 1 to 643 of SEQ ID NO:4.

In a preferred embodiment, the isolated polypeptide have an amino acid sequence which differs by five amino acids, e.g. by four amino acids, such as by three amino acids, by two amino acids, or by one amino acid from any of the amino acid sequences shown as amino acids 1 to 558 of SEQ ID NO:2 and 1 to 643 of SEQ ID NO:4.

In an embodiment of the second aspect of the invention, the isolated polypeptide is an alpha-L-arabinofuranosidase able to liberate arabinose from di-substituted xyloses, e.g. the alpha-L-arabinofuranosidase is active on xylose units of wheat arabinoxylan with arabinose attached to C2 and C3.

Alignments of sequences and calculation of homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for amino acid sequence comparison are used: GAP creation penalty of 3.0 and GAP extension penalty of 0.1. The relevant part of the amino acid sequence for the homology determination is the mature polypeptide, i.e. without the signal peptide.

Preferably, the polypeptides of the present invention comprise any of the amino acid sequences shown as amino acids 1 to 558 of SEQ ID NO:2 and 1 to 643 of SEQ ID NO:4, an allelic variant thereof, or a fragment thereof that has arabinofuranosidase activity. Obviously, the polypeptide of the invention may also consist of any of the amino acid sequences shown as amino acids 1 to 558 of SEQ ID NO:2 and 1 to 643 of SEQ ID NO:4.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In an embodiment of the invention, the isolated polypeptide is encoded by a nucleic acid sequence which hybridizes under low stringency conditions, preferably under medium stringency conditions, more preferably under high stringency conditions with (i) a complementary strand of any of the nucleic acid sequences shown as nucleotides 1 to 1677 of SEQ ID NO:1 and 46 to 1974 of SEQ ID NO:3, or (ii) a subsequence of (i) of at least 100 nucleotides (J. Sambrook, E. F. Fritsch, and T. Maniatus, 1989, *Molecular Cloning, A Laboratory Manual*, 2d edition, Cold Spring Harbor, N.Y.).

The subsequence of the complementary strand of any of the nucleic acid sequences shown as nucleotides 1 to 1677 of SEQ ID NO:1 and 46 to 1974 of SEQ ID NO:3, may be at least 100 nucleotides or preferably at least 200 nucleotides. Moreover, the subsequence should encode a polypeptide fragment which has arabinofuranosidase activity. The polypeptides may also be allelic variants or fragments of the polypeptides that have arabinofuranosidase activity.

The variants of the polypeptides specified comprising a substitution, deletion, and/or insertion of one or more amino acids. In a particular embodiment, the polypeptides are thermostable variants of the polypeptides specified.

The amino acid sequences of the variant polypeptides may differ from the amino acid sequence specified in amino acids 1 to 558 of SEQ ID NO:2 or 1 to 643 of SEQ ID NO:4 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The polypeptides referred to herein may comprise the amino acid sequence specified, or they may be an allelic variant thereof; or a fragment thereof that has the relevant enzyme activity. In one embodiment, the polypeptides comprise the amino acid sequence specified or an allelic variant thereof; or a fragment thereof that has the relevant enzyme activity. In another embodiment, the polypeptides consist of the amino acid sequence specified, or an allelic variant thereof; or a fragment thereof that has the relevant enzyme activity.

A fragment of a specified amino acid sequence is a polypeptide having one or more amino acids deleted from the amino and/or carboxyl terminus of this amino acid sequence. In one embodiment, a fragment contains at least 60 amino acid residues, or at least 68, or at least 70, or at least 75, or at least 100, or at least 150, or at least 160, or at least 170, or at least 180, or at least 190, or at least 200, or at least 210, or at least 220, or at least 240, or at least 260, or at least 280, or at least 300, or at least 310, or at least 320, or at least 330, or at least 334, or at least 350, or at least 375, or at least 400, or at least 425, or at least 430 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

A mature polypeptide or a mature amino acid sequence refers to that part of an amino acid sequence which remains after a potential signal peptide part has been cleaved off. And analogously, a mature polypeptide encoding part of a gene refers to that part of a gene, which corresponds to a mature polypeptide.

The nucleic acid sequence of any of SEQ ID NO:1 and SEQ ID NO:3 or a subsequence thereof, as well as the amino acid sequence of any of SEQ ID NO:2 and SEQ ID NO:4 or a fragment thereof, may be used to design a nucleic acid probe to identify and clone DNA encoding polypeptides having arabinofuranosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having arabinofuranosidase activity. Genomic or other DNA from such other organisms may be separated by agarose or polyacrylamide gel electrophoresis, or other separation techniques known by the skilled person. DNA from the libraries or the separated DNA may be transferred to and immobilized on nitrocellulose or other suitable carrier materials. In order to identify a clone or DNA which is homologous with SEQ ID NO:1 or SEQ ID NO:3, or a subsequence thereof, the carrier material is used in a Southern blot. For purposes of the present invention, hybridization indicates that the nucleic acid sequence hybridizes to a labeled nucleic acid probe corresponding to any of the nucleic acid sequences shown in SEQ ID NO:1 and SEQ ID NO:3, its complementary strand, or a subsequence thereof, under low to high stringency conditions. Molecules to which the nucleic acid probe hybridizes under these conditions are detected using X-ray film.

In another interesting embodiment, the nucleic acid probe is a nucleic acid sequence which encodes any of the (mature) polypeptides of SEQ ID NO:2 and SEQ ID NO:4, or a subsequence thereof. In a third interesting embodiment, the nucleic acid probe is any of SEQ ID NO:1 and SEQ ID NO:3. In a fourth interesting embodiment, the nucleic acid probe is any of the mature polypeptide coding regions of SEQ ID NO:1 and SEQ ID NO:3.

For long probes of at least 100 nucleotides in length, low to high stringency conditions are defined as prehybridization and hybridization at 42° C. in 5×SSPE, 0.3% SDS, 200 μg/ml sheared and denatured salmon sperm DNA, and either 25% formamide for low stringency, 35% formamide for medium stringency, or 50% formamide for high stringency, following standard Southern blotting procedures.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), even more preferably at least at 65° C. (high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

As indicated above, the polypeptide of the invention may be a polypeptide having any of the amino acid sequences of SEQ ID NO:2 and SEQ ID NO:4, or the mature polypeptide thereof, wherein one or more amino acid(s) has (have) been substituted by another (other) amino acid(s), wherein one or more amino acid(s) has (have) been deleted, and/or wherein one more amino acid(s) has (have) been inserted.

Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In general, it is preferred that the polypeptides of the invention have at least 20% of the arabinofuranosidase activity of the polypeptide having any of the amino acid sequences shown as amino acids 1 to 558 of SEQ ID NO:2 and amino acids 1 to 643 of SEQ ID NO:4. Particular preferred are polypeptides, which have at least 30%, such as at least 40%, e.g. at least 50%, preferably at least 60%, such as at least 70%, e.g. at least 80%, more preferred at least 90%, or at least 95% of the arabinofuranosidase activity of the polypeptide having any of the amino acid sequences shown as amino acids 1 to 558 of SEQ ID NO:2 and amino acids 1 to 643 of SEQ ID NO:4.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a fungal polypeptide, and more preferably a filamentous fungal polypeptide such as an Acremonium, Aspergillus, Aureobasidium, Cryptococcus, Filibasidium, Fusarium, Humicola, Magnaporthe, Meripilus, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In another preferred embodiment, the polypeptide is an Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Meripilus giganteus, Mucor miehei, Myceliophthora thermophila, Neurospora crassa, Penicillium purpurogenum, Trichoderma harzianum, Trichoderma koningii, Trichoderma longibrachiatum, Trichoderma reesei, or Trichoderma viride polypeptide.

In a preferred embodiment of the invention the polypeptide of the invention is derived from a strain within the Ascomycota, e.g., within the genus Humicola, such as within H. lanuginosa H. fuscoatra, H. grisea, H. lutea, H. nigrescens and in particular within H. insolens, or from as strain within Basidiomycota, such as within the genus Meripilus, such as within the M. giganteus.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In a particularly preferred embodiment of the invention the polypeptide of the invention is derived from the H. insolens strain described in WO9117243 and deposited Apr. 14, 1980 at the German Collection of Microorganisms and Cell cultures (DSM, Deutsche Sammlung von Mikroorganismen and Zellkulturen) Göttingen, Germany, under the DSM number 1800) in accordance with the provisions of the Budapest Treaty.

In a second particularly preferred embodiment of the invention the polypeptide of the invention is derived the specific strain of Meripilus giganteus having the accession number CBS 521.95 in Centraalbureau Voor Schimmelcultures (CBS), Uppsalalaan 8, 3584 CT Utrecht, The Netherlands (alternatively P.O. Box 85167, 3508 AD Utrecht, The Netherlands).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention.

In one interesting embodiment, the nucleic acid sequence has at least 80% identity with any of the nucleic acid sequences shown as nucleotides 1 to 1677 of SEQ ID NO:1 and 46 to 1974 of SEQ ID NO:2. Preferably, the nucleic acid sequence has at least at least 85%, at least 90%, at least 95%, at least 96%, at least 97%, at least 98%, or at least 99% identity with any of the nucleic acid sequences shown as nucleotides 1 to 1677 of SEQ ID NO:1 and 46 to 1974 of SEQ ID NO:2. In another interesting embodiment of the invention the nucleic acid sequence comprises any of the amino acid sequences shown as nucleotides 1 to 1677 of SEQ ID NO:1, an allelic variant thereof, or a fragment thereof capable of encoding a polypeptide according to the invention. Obviously, the nucleic acid sequence may consist of any of the amino acid sequences shown as nucleotides 1 to 1677 of SEQ ID NO:1 and 46 to 1974 of SEQ ID NO:2.

The present invention also encompasses nucleic acid sequences which encode a polypeptide having any of the amino acid sequences of SEQ ID NO:2 or SEQ ID NO:4, or the mature polypeptides thereof, which differ from SEQ ID NO:1 or SEQ ID NO:3 by virtue of the degeneracy of the genetic code. The present invention also relates to subsequences of SEQ ID NO:1 or SEQ ID NO:3 which encode fragments of SEQ ID NO:2 or SEQ ID NO:4 that have arabinofuranosidase activity. A subsequence of SEQ ID NO:1 or SEQ ID NO:3 is a nucleic acid sequence encompassed by nucleotides 1 to 1677 of SEQ ID NO:1 or nucleotides 46 to 1974 of SEQ ID NO:3 except that one or more nucleotides from the 5' and/or 3' end have been deleted.

The present invention also relates to isolated nucleic acid sequences encoding a polypeptide of the present invention, which hybridize under low stringency conditions, preferably under medium stringency conditions, more preferably under high stringency conditions, with (i) a complementary strand of any of the nucleic acid sequences shown as nucleotides 1 to 1677 of SEQ ID NO:1 and 46 to 1974 SEQ ID NO:3, or (ii) a subsequence of (i) of at least 100 nucleotides. The present invention also relates to complementary strands of (i) and (ii).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Humicola insolens* or from a strain of *Meripilus giganteus*, or another or related organism and may, for example, be an allelic or species variant of the polypeptide encoding region of the nucleic acid sequence.

An isolated nucleic acid sequence can, for example, be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

For purposes of the present invention, the degree of identity between two nucleic acid sequences is determined as described above.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for arabinofuranosidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Nucleic Acid Constructs

The present invention also relates to nucleic acid constructs comprising a nucleic acid sequence of the present invention operably linked to one or more control sequences capable of directing the expression of the polypeptide in a suitable host cell.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell.

Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *Escherichia coli* (*E. coli*), and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides.

A vector comprising a nucleic acid sequence of the present invention is introduced into a host cell so that the vector is maintained as a chromosomal integrant or as a self-replicating extra-chromosomal vector as described earlier. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell. In a preferred embodiment, the host cell is a fungal cell. "Fungi" as used herein includes the phyla *Ascomycota*, *Basidiomycota*, *Chytridiomycota*, and *Zygomycota* (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred embodiment, the yeast host cell is a *Candida*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*.

In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens*, *Humicola lanuginosa*, *Mucor miehei*, *Myceliophthora thermophila*, *Neurospora crassa*, *Peni-* cillium purpurogenum, Thielavia terrestris, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention, the method comprising (a) cultivating a strain from the genus Humicola or the genus Meripilus. to produce a supernatant comprising the polypeptide; and (b) recovering the polypeptide. Preferably, the strain is of the species Humicola insolens or the species Meripilus giganteus.

The present invention also relates to a method for producing a polypeptide of the invention, the method comprising (a) cultivating a recombinant host cell as described above under conditions conducive to the production of the polypeptide, and (b) recovering the polypeptide from the cells and/or the culture medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Expression of the Enzymes in Plants

A DNA sequence encoding a polypeptide of interest, such as an arabinofuranosidase of the present invention, may be transformed and expressed in transgenic plants as described below.

The transgenic plant can be dicotyledonous or monocotyledonous, for short a dicot or a monocot. Examples of monocot plants are grasses, such as meadow grass (blue grass, Poa), forage grass such as Festuca, Lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous plants (family Brassicaceae), such as cauliflower, oil seed rape and the closely related model organism Arabidopsis thaliana.

Examples of plant parts are stem, callus, leaves, root, fruits, seeds, and tubers as well as the individual tissues comprising these parts, e.g. epidermis, mesophyll, parenchyme, vascular tissues, meristems. In the present context, also specific plant cell compartments, such as chloroplast, apoplast, mitochondria, vacuole, peroxisomes and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts e.g. embryos, endosperms, aleurone and seeds coats.

Also included within the scope of the invention are the progeny of such plants, plant parts and plant cells.

The transgenic plant or plant cell expressing the polypeptide of interest may be constructed in accordance with methods known in the art. In short the plant or plant cell is constructed by incorporating one or more expression constructs encoding the polypeptide of interest into the plant host genome and propagating the resulting modified plant or plant cell into a transgenic plant or plant cell.

Conveniently, the expression construct is a DNA construct which comprises a gene encoding the polypeptide of interest in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g. on the basis of when, where and how the enzyme is desired to be expressed. For instance, the expression of the gene encoding the enzyme of the invention may be constitutive or inducible, or may be developmental, stage or tissue specific, and the gene product may be targeted to a specific cell compartment, tissue or plant part such as seeds or leaves. Regulatory sequences are, e.g. described by Tague et al, Plant, Phys., 86, 506, 1988.

For constitutive expression the 35S-CaMV, the maize ubiquitin 1 and the rice actin 1 promoter may be used (Franck et al. 1980. Cell 21: 285-294, Christensen A H, Sharrock R A and Quail 1992. Maize polyubiquitin genes: structure, thermal perturbation of expression and transcript splicing, and promoter activity following transfer to protoplasts by electroporation. Plant Mo. Biol. 18, 675-689.; Zhang W, McElroy D. and Wu R 1991, Analysis of rice Act1 5' region activity in transgenic rice plants. Plant Cell 3, 1155-1165). Organ-specific promoters may, e.g. be a promoter from storage sink tissues such as seeds, potato tubers, and fruits (Edwards & Coruzzi, 1990. Annu. Rev. Genet. 24: 275-303), or from metabolic sink tissues such as meristems (Ito et al., 1994. Plant Mol. Biol. 24: 863-878), a seed specific promoter such as the glutelin, prolamin, globulin or albumin promoter from rice (Wu et al., Plant and Cell Physiology Vol. 39, No. 8 pp. 885-889 (1998)), a *Vicia faba* promoter from the legumin B4 and the unknown seed protein gene from *Vicia faba* described by Conrad U. et al, Journal of Plant Physiology Vol. 152, No. 6 pp. 708-711 (1998), a promoter from a seed oil body protein (Chen et al., Plant and cell physiology vol. 39, No. 9 pp. 935-941 (1998), the storage protein napA promoter from *Brassica napus*, or any other seed specific promoter known in the art, e.g. as described in WO 91/14772. Furthermore, the promoter may be a leaf specific promoter such as the rbcs promoter from rice or tomato (Kyozuka et al., Plant Physiology Vol. 102, No. 3 pp. 991-1000 (1993), the chlorella virus adenine methyltransferase gene promoter (Mitra, A. and Higgins, D W, Plant Molecular Biology Vol. 26, No. 1 pp. 85-93 (1994), or the aldP gene promoter from rice (Kagaya et al., Molecular and General Genetics Vol. 248, No. 6 pp. 668-674 (1995), or a wound inducible promoter such as the potato pin2 promoter (Xu et al, Plant Molecular Biology Vol. 22, No. 4 pp. 573-588 (1993). Likewise, the promoter may inducible by abiotic treatments such as temperature, drought or alterations in salinity or induced by exogenously applied substances that activate the promoter e.g. ethanol, oestrogens, plant hormones like ethylene, abscisic acid and gibberellic acid and heavy metals.

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including *Agrobacterium*-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15-38), and can also be used for transforming monocots, although other transformation methods often are used for these plants. Presently, the method of choice for generating transgenic monocots supplementing the *Agrobacterium* approach is particle bombardment (microscopic gold or tungsten particles coated with the transforming DNA) of embryonic calli or developing embryos (Christou, 1992. Plant J. 2: 275-281; Shimamoto, 1994. Curr. Opin. Biotechnol. 5: 158-162; Vasil et al., 1992. Bio/Technology 10: 667-674). An alternative method for transformation of monocots is based on protoplast transformation as described by Omirulleh S, et al., Plant Molecular biology Vol. 21, No. 3 pp. 415-428 (1993).

Following transformation, the transformants having incorporated the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

Use of Arabinofuranosidases

The present invention also relates to use of the polypeptides of the invention, i.e. the arabinofuranosidases, in various industrial application, e.g. in biomass conversion, such as in production of fuel ethanol from cellulose containing biomass, in production of fuel and/or potable ethanol from starch, in mashing for beer production, in a dough for bread making, or in manufacture of an animal feed product.

The invention furthermore provides a process wherein a arabinoxylan containing substrate and/or a biomass is contacted with an arabinofuranosidase capable of releasing arabinose from di-substituted xyloses. Preferably the alpha-L-arabinofuranosidase is an arabinofuranosidase of GH43. The alpha-L-arabinofuranosidase of GH43 is preferably derived of baterial, of fungal or of plant origin. Preferably the arabinoxylan containing substrate and/or the biomass is selected from the list consisting of herbaceous and/or woody energy crops, agricultural food and feed crops, animal feed products, tubers, roots, stems, legumes, cassava peels, cocoa pods, rice husks and/or hulls, rice bran from rice polishing, cobs, straw, hulls and/or husks from cereal grain, pressed sugar cane stalk, sugar beet pulp, locust bean pulp, vegetable or fruit pomaces, cereals or whole grain agricultural crop waste, straw, stalks, leaves, corn bran, husks, cobs, rind, shells, pods, wood waste, bark, shavings, sawdust, wood pulp, pulping liquor, waste paper, cardboard, construction and demolition wood waste, industrial or municipal waste water solids or sludge, manure, by-product from brewing and/or fermentation processes, wet distillers grain, dried distillers grain, spent grain, vinasse and bagasse.

The present invention also relates to compositions comprising the polypeptides of the invention, i.e. the arabinofuranosidase, as well as to uses of such compositions.

Materials and Methods

Arabinose and xylose were purchased from Merck (Darmstadt, Germany). Water soluble and water insoluble wheat arabinoxylans were obtained from Megazyme (Bray, County Wicklow, Ireland).

Enzymes

The alpha-L-arabinofuranosidases were cloned using basic molecular techniques (Sambrook et al., 1989, *Molecular Cloning, A Laboratory Manual*, 2d edition, Cold Spring Harbor, N.Y., Christgau et al. 1995, Curr. Genet. 27, 135-141, Ausubel et al., 2003, Curr. Prot. Mol. Biol., John Wiley & Sons, Cambridge, USA,).

The *Bifidobacterium adolescentis* alpha-L-arabinofuranosidases of Van Laere et al. (1997) and Van den Broek et al. (2005) was obtained from Megazyme (Ireland).

Shearzyme (GH10) and Pentopan Mono (GH11), mono-component endo-1,4-β-xylanase preparations produced by *Aspergillus aculeatus* and *Thermomyces lanuginosus*, respectively, were commercial products from Novozymes A/S (Bagsværd, Denmark).

Preparation of Specific Arabinoxylan Polymers and Oligosaccharides

Doubly substituted arabinoxylan was prepared by incubating soluble wheat arabinoxylan (1 g) in 0.1 M acetate buffer (100 mL), pH 6.0 with 0.167 g α-L-arabinofuranosidase from *Meripilus giganteus* (GH51)·kg$^{-1}$ water soluble wheat arabinoxylan for 48 hours at 30° C. Singly substituted arabinoxylan was prepared by incubating water soluble wheat arabinoxylan (1 g) in 0.1 M acetate buffer (42 mL), pH 6.0 with 0.147 g α-L-arabinofuranosidase from *Humicola insolens* (GH43)·kg$^{-1}$ water soluble wheat arabinoxylan for 48 hours at 30° C. To halt the enzymatic reactions the mixtures were heated to 100° C. for 10 min. Arabinoxylan polymers were precipitated by addition of ethanol (126 ml). The precipitates were filtered (Miracloth) and dried in vacuum Oligosaccharides containing arabinosyl groups linked to terminal (1→3) were prepared by incubating the water insoluble wheat arabinoxylan (1 g) in 0.1 M acetate buffer (100 mL), pH 6.0 with 6.67 g Shearzyme (xylanase GH10)·kg$^{-1}$ water insoluble wheat arabinoxylan for 2 hours at 30° C. Oligosaccharides containing arabinosyl groups linked to internal (1→3) were prepared by incubating water insoluble wheat arabinoxylan (1 g) in 0.1 M acetate buffer (100 mL), pH 6.0 with 0.03 g Pentopan Mono (xylanase GH11)·kg$^{-1}$ water insoluble wheat arabinoxylan for 2 hours at 30° C. Oligosaccharides containing arabinosyl groups linked to internal (1→2) were prepared by incubating water insoluble wheat arabinoxylan (1 g) in 0.1 M acetate buffer (100 mL), pH 6.0 with 0.03 g Pentopan Mono (xylanase GH11)·kg$^{-1}$ water insoluble wheat arabinoxylan and alpha-L-arabinofuranosidase from *H. insolens* (GH43)·kg$^{-1}$ water soluble wheat arabinoxylan for 2 hours at 30° C. To halt the enzymatic reactions the mixtures were heated to 100° C. for 10 min. The arabinoxylo-oligosaccharides were concentrated on a rotary evaporator and evaluated by $^1$H-NMR.

Assay for Activity Towards Alpha-L-Arabinofuranosidase Activity

Alpha-L-arabinofuranosidase activity may be assessed as described by Poutanen et al. (Appl. Microbiol. Biotechnol. 1988, 28, 425-432) using 5 mM p-nitrophenyl alpha-L-arabinofuranoside as substrates. The reactions may be carried out in 50 mM citrate buffer at pH 6.0, 40° C. with a total reaction time of 30 min. The reaction is stopped by adding 0.5 ml of 1 M sodium carbonate and the liberated p-nitrophenol is measured at 405 nm. Activity is expressed in U/ml.

Assay for Activity Towards C2- and C3-Di-Substituted Xylan

Medium viscosity water-soluble wheat arabinoxylan (Megazyme, Bray, Ireland) was treated with an alpha-arabinofuranosidase of GH51 from *Meripilus giganteus* (SEQ ID NO:2) to remove single alpha-arabinofuranosyl substituents attached to the C(O)-3 arabinose of the arabinoxylan in order to produce an di-substituted arabinoxylan substrate with arabinofuranosyl substituents attached to both C(O)-2,3 of the xylose residues. The substrate was dialysed and freeze dried.

A 0.1% solution of the di-substituted arabinoxylan was prepared and the alpha-arabinofuranosidase activity was measured by mixing 0.1 ml enzyme, 0.9 ml buffer (0.12 M Succinic acid, pH 6.0) and 1.0 ml substrate solution in an eppendorf tube. The eppendorf tube was incubated at 60° C. for 1 hour with shaking. The amount of liberated arabinose was measured by HPAEC (high-performance anion-exchange chromatography).

HPAEC

Hydrolysates (10 μl) were applied onto a Dionex BioLC system fitted with a Dionex CarboPac™ PA1 guard column (4×250 mm) (Dionex Corporation, Sunnyvale, Calif., USA) combined with a CarboPac™ PA1 precolumn (4×50 mm). The monosaccharides were separated isocratically with 10 mM KOH for 15 min, flow: 1 mL·min$^{-1}$. Monosaccharides were detected by a pulsed electrochemical detector in the pulsed amperiometric detection mode. The potential of the electrode was programmed for +0.1 V (t=0-0.4 s) to −2.0 V (t=0.41-0.42 s) to 0.6 V (t=0.43 s) and finally −0.1 V (t=0.44-0.50 s), while integrating the resulting signal from t=0.2-0.4 s. A mixture of arabinose and xylose (concentration of each component: 0.0025-0.1 g·L$^{-1}$) was used as standard.

$^1$H-NMR Analysis

All degradation products were lyophilized twice from 99.9% D$_2$O and re-dissolved in 99.9% D$_2$O. Some hydrolysates were dialyzed (Spectra/Por membrane molecular weight cut-off 1000) to remove free arabinose prior to the spectral analysis. The $^1$H-NMR spectra were recorded at 30° C. in a Varian Mercury-VX instrument operated at 400 MHz and equipped with a 4-nucleus auto-switchable probe. Data were collected over 128-512 scans and the HDO signal was used as a reference signal (4.67 ppm).

EXAMPLES

Example 1

Wheat arabinoxylan comprises arabinofuranoside as a monosubstituent linked to the 3-position of internal xylose (A) and arabinofuranoside linked to the 3- (B) and 2-position (C) on di-substituted xylose, respectively. Substrates were produced each comprising only one of the 3 types of arabinofuranoside linkages. The activity of arabinofuranosidases towards these substrates was investigated using $^1$H NMR.

TABLE 1

Origin, families, and molecular mass of alpha-L-arabinofuranosidase activities

| Origin | Family | Mol mass (kDa) |
|---|---|---|
| *H. insolens* (SEQ ID NO: 2) | GH43 | ~62 |
| *M. giganteus* (SEQ ID NO: 4) | GH51 | ~69 |
| *B. adolescentis* | GH43 | ~60 |
| *H. insolens* | GH51 | ~94 |

TABLE 2

Activity on selected arabinoxylan polymers, incubation at pH 6, 40° C. for 2 hrs.

| | | Enzyme | | | |
|---|---|---|---|---|---|
| Substrate | Linkage | *H. insolens* (GH43) | *B. adolescentis* (GH43) | *H. insolens* (GH51) | *M. giganteus* (GH51) |
| Intact arabinoxylan | Mono-substituted (1→3) | — | — | x | xx |
| | Di-substituted (1→2) | — | — | — | — |
| | Di-substituted (1→3) | xx | x | — | — |

TABLE 2-continued

Activity on selected arabinoxylan polymers, incubation at pH 6, 40° C. for 2 hrs.

| Substrate | Linkage | H. insolens (GH43) | B. adolescentis (GH43) | H. insolens (GH51) | M. giganteus (GH51) |
|---|---|---|---|---|---|
| Di-substituted arabinoxylan | Di-substituted (1→2) | — | — | — | — |
|  | Di-substituted (1→3) | xx | xx | — | — |
| Mono-substituted arabinoxylan | Mono-substituted (1→2) | — | — | xx | xx |
|  | Mono-substituted (1→3) | — | — | xx | xx | xx refers to more than 75% hydrolysis, x(x) to 50-75% hydrolysis, x to 25-50% hydrolysis and (x) to 5-25% hydrolysis. — refers to no detectable hydrolysis

Example 2

Soluble wheat arabinoxylan was incubated with 0.1 g enzyme protein per kg DM of alpha-L-arabinofuranosidase from *H. insolens* (GH43), *B. adolescentis* (GH43), *H. insolens* (GH51), and *M. giganteus* (GH51) for 24 hrs. The released arabinose was measured. Results are expressed in mg arabinose per g water soluble wheat arabinoxylan, as the average of triplicate determinations, coefficient of variation on mean <6.4.

TABEL 3

Released arabinose from soluble wheat arabinoxylan treated with alpha-L-arabinofuranosidase.

| Origin | Reaction conditions | |
|---|---|---|
|  | pH 6, 40° C. | pH 5, 50° C. |
| H. insolens (GH43) | 128.0 a | 147.0 a |
| M. giganteus (GH51) | 48.15 c | 121.0 b |
| B. adolescentis (GH43) | 63.43 b | 4.833 d |
| H. insolens (GH51) | 20.75 d | 18.47 c |

Example 3

Arabionofuranosidases may be applied in animal feed compositions to increase digestibility. Corn arabinoxylan is heavily di-substituted with arabinose. In order to facilitate the xylan degradation it is advantageous to remove as many as possible of the arabinose substituents. The in vitro degradation of arabinoxylans in a corn based diet supplemented with the GH51 arabinofuranosidase from *Humicola insolens* and a commercial xylanase derived from *Termomyces lanuginosus* was studied in an in vitro digestion system.

Conditions for the Vitro Digestion System:
Substrate: 800 mg 30:70 Soy bean meal/Corn diet milled and pre-blended
pH: pH 5, 4 and 3 (gastric) and 4.0 (transition step) followed by a small intestinal step at pH 6.8
Pepsin: 3000 U/g diet.
Pancreatin 8 mg/g diet
Temperature: 40° C.
Number of replicates: 4
Enzyme dosage: Arabinofuranosidase and xylanase 50 and 67 mg EP/kg diet respectively Samples were precipitated with 80% ethanol, centrifuged and supernatant discarded. The pellet was washed in 80% ethanol and centrifuged and supernatant discarded. The pellet was dissolved in acetate buffer (pH 5) and starch was removed before dietary fibre analysis.

TABLE 4

Content of arabinose and xylose in residual total non-starch polysaccharide residues after in vitro digestion

| | Non-starch polysaccharide residues (% of dry matter) | |
|---|---|---|
|  | Arabinose | Xylose |
| Control | 1.78a | 2.06a |
| Arabinofuranosidase from Humicola insolens | 1.71a | 1.93a |
| Xylanase from Thermomyces lanuginosus | 1.68a | 1.81b |
| Xylanase + arabinofuranosidase | 1.60b | 1.78b |

Average values within a column not sharing a common letter index differ with statistical significance ($P < 0.05$).

The invention claimed is:

1. A nucleic acid construct comprising a nucleic acid sequence encoding a polypeptide having arabinofuranosidase activity, wherein the nucleic acid sequence is operably linked to one or more heterologous control sequences capable of directing the expression of the polypeptide in a suitable expression host, and wherein the polypeptide is selected from the group consisting of:
   (a) a polypeptide with at least 95% sequence identity to the mature polypeptide of SEQ ID NO: 2; and
   (b) a polypeptide which is encoded by a nucleic acid sequence which hybridizes under high stringency conditions with the full complement of the nucleic acid sequence of nucleotides 55-1677 of SEQ ID NO: 1; wherein the high stringency conditions are defined as prehybridization and hybridization at 42° C. in 5×SSPE, 0.3% SDS, 200 micrograms/mL sheared and denatured salmon sperm DNA, and 50% formamide for high stringency, following standard Southern blotting procedures, followed by washing three times each for 15 minutes using 2×SSC, 0.2% SDS at 65° C.

2. The nucleic acid construct of claim 1, wherein the polypeptide has at least 95% sequence identity to the mature polypeptide of SEQ ID NO: 2.

3. The nucleic acid construct of claim 1, wherein the polypeptide has at least 97% sequence identity to the mature polypeptide of SEQ ID NO: 2.

4. The nucleic acid construct of claim 1, wherein the polypeptide comprises the mature polypeptide of SEQ ID NO: 2.

5. The nucleic acid construct of claim 1, wherein the polypeptide is a fragment of the mature polypeptide of SEQ ID NO: 2 and has arabinofuranosidase (EC 3.2.1.55) activity, wherein the fragment has one or more amino acids deleted from the amino and/or carboxyl terminus of the mature polypeptide of SEQ ID NO: 2 and has at least 430 amino acids of the mature polypeptide of SEQ ID NO: 2.

6. The nucleic acid construct of claim 1, wherein the polypeptide is native to a strain of Humicola.

7. The nucleic acid construct of claim 1, wherein the polypeptide is native to a strain of Humicola insolens.

8. The nucleic acid construct of claim 1, wherein the polypeptide comprises amino acids 19 to 558 of SEQ ID NO: 2 and exhibits arabinofuranosidase activity.

9. A recombinant expression vector comprising the nucleic acid construct of claim 1.

10. A recombinant host cell transformed with the nucleic acid construct of claim 1.

11. A method for producing a polypeptide having arabinofuranosidase activity, comprising cultivating the recombinant host cell of claim 10 under conditions conducive for production of the polypeptide, and recovering the polypeptide.

12. A recombinant host cell transformed with a nucleic acid sequence encoding a polypeptide having arabinofuranosidase activity, wherein the nucleic acid sequence is operably linked to one or more heterologous control sequences and wherein the polypeptide is selected from the group consisting of:
   (a) a polypeptide with at least 95% sequence identity to the mature polypeptide of SEQ ID NO: 2; and
   (b) a polypeptide which is encoded by a nucleic acid sequence which hybridizes under high stringency conditions with the full complement of the nucleic acid sequence of nucleotides 55-1677 of SEQ ID NO: 1; wherein the high stringency conditions are defined as prehybridization and hybridization at 42° C. in 5×SSPE, 0.3% SDS, 200 micrograms/mL sheared and denatured salmon sperm DNA, and 50% formamide for high stringency, following standard Southern blotting procedures, followed by washing three times each for 15 minutes using 2×SSC, 0.2% SDS at 65° C.

13. A method for producing a polypeptide having arabinofuranosidase activity, comprising cultivating the recombinant host cell of claim 12 under conditions conducive for production of the polypeptide, and recovering the polypeptide.

* * * * *